(12) United States Patent
Dakka et al.

(10) Patent No.: US 8,921,609 B2
(45) Date of Patent: Dec. 30, 2014

(54) OXIDATION OF HYDROCARBONS

(75) Inventors: Jihad M. Dakka, Whitehouse Station, NJ (US); Stephen Zushma, Clinton, NJ (US); Nicolas P. Coute, Houston, TX (US); Francisco M. Benitez, Cypress, TX (US); Edmund J. Mozeleski, Califon, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 301 days.

(21) Appl. No.: 13/498,998

(22) PCT Filed: Sep. 30, 2010

(86) PCT No.: PCT/US2010/050970
§ 371 (c)(1),
(2), (4) Date: May 9, 2012

(87) PCT Pub. No.: WO2011/066037
PCT Pub. Date: Jun. 3, 2011

(65) Prior Publication Data
US 2012/0215025 A1    Aug. 23, 2012

Related U.S. Application Data

(60) Provisional application No. 61/264,399, filed on Nov. 25, 2009.

(30) Foreign Application Priority Data

Jan. 13, 2010 (EP) ..................................... 10150597

(51) Int. Cl.
C07C 409/00 (2006.01)
C07C 29/50 (2006.01)
C07C 407/00 (2006.01)

(52) U.S. Cl.
CPC ............... C07C 29/50 (2013.01); C07C 407/00 (2013.01); C07C 2101/14 (2013.01)
USPC ........... 568/573; 568/385; 568/558; 568/568; 568/570; 568/741

(58) Field of Classification Search
None
See application file for complete search history.

(56) References Cited

U.S. PATENT DOCUMENTS

| | | | |
|---|---|---|---|
| 6,528,658 B1 | 3/2003 | Miura et al. | |
| 6,720,462 B2 | 4/2004 | Kuhnle et al. | |
| 6,852,893 B2 | 2/2005 | Kuhnle et al. | |
| 7,038,089 B2 | 5/2006 | De Frutos Escrig et al. | |
| 2002/0169331 A1* | 11/2002 | Miura et al. | 552/1 |
| 2003/0083527 A1 | 5/2003 | Kuhnle et al. | |
| 2004/0014985 A1 | 1/2004 | Sugahara | |
| 2005/0043559 A1 | 2/2005 | Marhold et al. | |
| 2007/0265476 A1* | 11/2007 | Dakka et al. | 568/385 |
| 2008/0269507 A1 | 10/2008 | Kajikawa et al. | |
| 2010/0222609 A1 | 9/2010 | Dakka et al. | |

FOREIGN PATENT DOCUMENTS

| | | |
|---|---|---|
| JP | 2004-035460 | 2/2004 |
| WO | 99/47485 | 9/1999 |
| WO | 2009/025939 | 2/2009 |
| WO | 2010/098916 | 9/2010 |

OTHER PUBLICATIONS

Arends et al (Tetrahedron, 2002, 58, pp. 9055-9061).*
Y. Ishii et al., "*Recent Progress in Aerobic Oxidation of Hydrocarbons by N-hydroxyimides*", Catalysis Today, 2006, vol. 117, pp. 105-113.
T. Iwahama et al., "*Aerobic Oxidation of Alcohols to Carbonyl Compounds Catalyzed by N-Hydroxyphthalimide (NHPI) Combined with Co (acac)$_3$*", Tetrahedron Letters, 1995, vol. 36, No. 38, pp. 6923-6926.
S. Sakaguchi et al., "*Oxidation of Organic Substrates with Molecular Oxygen Catalyzed by Vanadomolybdophosphate (NPV$_6$Mo$_6$) Combined with N-Hydroxyphthalimide (NHPI)*", Technology Reports of Kansai University, 1996, No. 38, pp. 123-131.

* cited by examiner

*Primary Examiner* — Sudhakar Katakam
(74) *Attorney, Agent, or Firm* — Siwen Chen; Stephen A. Baehl

(57) ABSTRACT

In a process for oxidizing a hydrocarbon, the hydrocarbon is contacted with oxygen in the presence of an N-substituted cyclic imide and under conditions to oxidize the hydrocarbon to produce an oxidized hydrocarbon product and at least one decomposition product of the N-substituted cyclic imide. At least a portion of the at least one decomposition product is contacted with hydroxylamine or a salt thereof under conditions to convert the at least one decomposition product back to said imide.

24 Claims, 1 Drawing Sheet

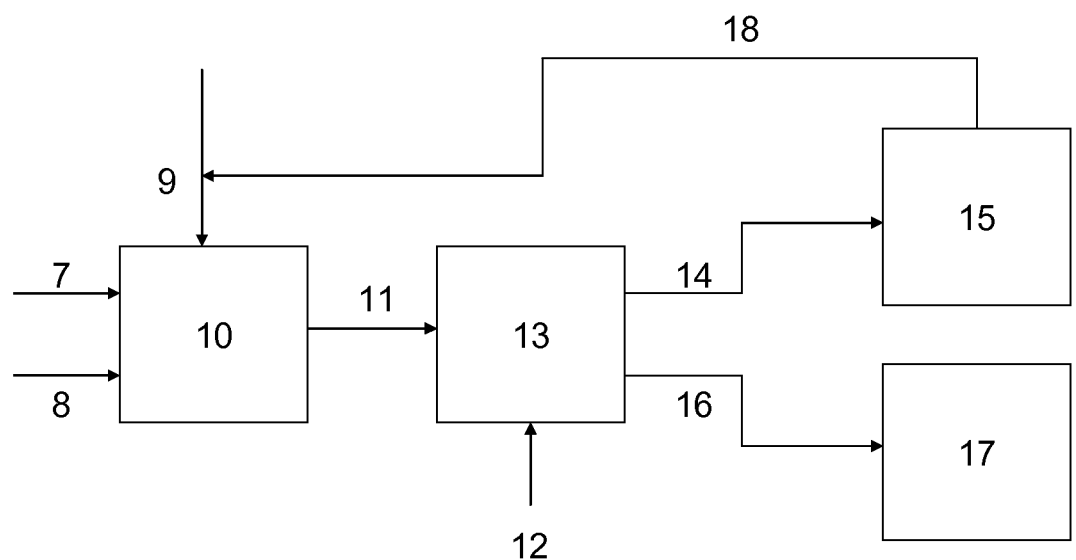

OXIDATION OF HYDROCARBONS

CROSS REFERENCE TO RELATED APPLICATIONS

This application claims priority to U.S. Provisional Application Ser. No. 61/264,399 filed Nov. 25, 2009 and PCT Application No. PCT/US2010/050970 filed on Sep. 30, 2010, the disclosures of which are fully incorporated herein by their reference.

FIELD

The present invention relates to a process for oxidizing hydrocarbons and, in particular, alkylaromatic hydrocarbons to produce, for example, phenol and substituted phenols.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas the oxidation of alkylaromatic hydrocarbons is used to produce phenol, a precursor in the production of polycarbonates and epoxy resins.

Oxidation of hydrocarbons can be conducted using well-known oxidizing agents, such as $KMnO_4$, $CrO_3$ and $HNO_3$. However, these oxidizing agents have the disadvantage of being relatively expensive, and moreover their use is accompanied by the production of unwanted coupling products which can represent disposal problems.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autooxidation of hydrocarbons. Thus, for example, the oxidation of cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom from a further hydrocarbon. In addition to metal salts, however, organic molecules can also act as free-radical initiators.

However, it is a disadvantage of these processes that the selectivity decreases greatly with increasing conversion and therefore the processes must be operated at a very low level of conversion. Thus, for example, the oxidation of cyclohexane to cyclohexanol/cyclohexanone is carried out at a conversion of 10 to 12% so that the selectivity is 80 to 85% ("Industrielle Organische Chemie" [Industrial Organic Chemistry] 1994, 261, VCH-Verlag, D-69451 Weinheim).

An alternative to metal salt catalysts are organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a catalyst, typically an N-hydroxycarbodiimide catalyst, such as N-hydroxyphthalimide (NHPI). The process is conducted at a temperature between 0° C. and 500° C. and a pressure between atmospheric and 100 bar (100 and 10,000 kPa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene and sec-butylbenzene.

U.S. Pat. No. 7,038,089 discloses a process for preparing a hydroperoxide from a hydrocarbon selected from the group consisting of primary hydrocarbons, secondary hydrocarbons and mixtures thereof, which process comprises oxidizing the hydrocarbon at a temperature in the range between 130 and 160° C. with an oxygen-containing gas in a reaction mixture containing the hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, cymene, ethylbenzene, diisopropylbenzene, cyclohexylbenzene, tetrahydronaphthalene (tetraline), indan, etc.). The amount of the cyclic imide compound used may be adduct or salt from 0.0001 to 1%, preferably from 0.0005 to 0.5%, by weight based on the reaction mixture, whereas the amount of the alkali metal compound may be from 0.000005 to 0.01%, preferably from 0.00001 to 0.005%, by weight based on the reaction mixture.

However, although current work has continued to demonstrate the utility of cyclic imides as hydrocarbon oxidation catalysts, it has also shown that their application in a commercial process requires further development. In particular, cyclic imides, such as N-hydroxyphthalimide, are expensive and are readily hydrolyzed under the conditions of the oxidation reaction. Moreover, unreacted imide catalysts and their decomposition products (acids and ethers) can pose significant problems to downstream reactions, such as hydroperoxide cleavage. Thus the successful application of cyclic imides to the oxidation of hydrocarbons will require treatment of the oxidation effluent to remove unreacted imides and their decomposition products and, if possible, recovery of the valuable unreacted imides.

International Application No. WO 2009/025939 discloses a process for oxidizing a hydrocarbon to the corresponding hydroperoxide, alcohol, ketone, carboxylic acid or dicarboxylic acid, in which the hydrocarbon is contacted with an oxygen-containing gas in the presence of a catalyst comprising a cyclic imide to produce an effluent comprising an oxidized hydrocarbon product and unreacted imide catalyst. The effluent is then treated with an aqueous solution of a base, particularly an alkali metal carbonate and/or hydrogen carbonate, to produce an aqueous phase comprising a salt of the unreacted imide and an organic phase comprising the oxidized hydrocarbon product. The aqueous phase is then acidified to precipitate the unreacted imide catalyst, which is then recovered and recycled to the oxidation step.

According to the present invention, it has now been found that as an alternative, or in addition, to capturing the unreacted imide with a base and recycling the imide to the hydrocarbon oxidation step, it is possible to feed the captured imide to an imide manufacturing process and thereby enhance the imide yield of the process.

SUMMARY

In one aspect, the invention resides in a process for oxidizing a hydrocarbon the process comprising:

(a) contacting a hydrocarbon in the presence of an N-substituted cyclic imide and under conditions to oxidize said hydrocarbon and produce an oxidized hydrocarbon product and at least one decomposition product of the N-substituted cyclic imide; and (b) contacting at least part of the at least one decomposition product with a first reactant selected from a hydroxylamine or a salt thereof under conditions to convert at least part of the at least one decomposition product back to said imide.

In various embodiments, the decomposition product is contacted with a second reactant selected from an acid or anhydride thereof. In one embodiment, the acid or anhydride thereof is a polycarboxylic acid or anhydride.

In one embodiment, the process further comprises (a) treating the oxidized hydrocarbon product, unreacted N-substituted cyclic imide and at least one decomposition product of the N-substituted cyclic imide with a base prior to the contacting (b) to convert at least part of said unreacted imide and said decomposition products to an adduct or salt; and (b) removing at least a portion of the adduct or salt from the oxidized hydrocarbon product.

In one embodiment, the hydrocarbon comprises an alkylaromatic compound of general formula (I):

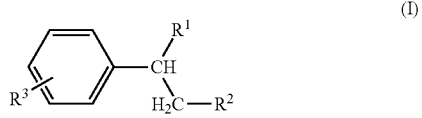

(I)

wherein $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, and $R^3$ represents hydrogen, one or more alkyl groups having from 1 to 4 carbon atoms or a cyclohexyl group.

Conveniently, said alkylaromatic compound of general formula (I) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

In another embodiment, hydrocarbon comprises an alkane, such as isobutane, or cycloalkane, such as cyclohexane.

Conveniently, said N-substituted cyclic imide obeys the general formula (II):

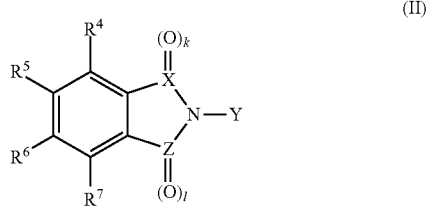

(II)

wherein each of $R^4$, $R^5$, $R^6$, and $R^7$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2.

In one embodiment, said N-substituted cyclic imide comprises N-hydroxyphthalimide.

In one embodiment, said base comprises ammonia and said amide salt is precipitated from said effluent.

In another embodiment, said base comprises an aqueous ammonium hydroxide or hydroxylamine solution and said adduct or salt is dissolved in said aqueous solution.

In a further embodiment, said base comprises an aqueous solution of a metal carbonate and/or hydrogen carbonate and said adduct or salt is dissolved in said aqueous solution.

In yet a further embodiment, said base comprises pyridine and said adduct or salt is precipitated from said effluent.

BRIEF DESCRIPTION OF THE DRAWINGS

FIG. 1 is a flow diagram of a hydrocarbon oxidation process according to one embodiment of the invention.

DETAILED DESCRIPTION

Described herein a process for oxidizing a hydrocarbon to at least one of the corresponding hydroperoxide, alcohol, ketone, carboxylic acid or dicarboxylic acid. The process comprises contacting a reaction medium comprising a hydrocarbon with an oxygen-containing gas in the presence of a catalyst comprising a cyclic imide and under conditions to oxidize said hydrocarbon. The oxidation reaction produces an effluent comprising the oxidized hydrocarbon product and decomposition products of the N-substituted cyclic imide.

In various embodiments, the decomposition products are then contacted with a first reactant selected from hydroxylamine or a salt thereof under conditions to convert at least a portion of the at least one decomposition product back to said imide.

In various embodiments, one or more of the oxidized hydrocarbon product, unreacted N-substituted cyclic imide and decomposition product of the N-substituted cyclic imide are treated with a base before contacting with the first reactant to convert at least a portion of the unreacted imide and the decomposition product to an adduct or salt. The adduct or salt may then be separated and, optionally, fed to a process for synthesizing the cyclic imide thereby increasing the synthesis yield.

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexyl hydroperoxide, cyclohexanol and cyclohexanone and the selective oxidation to the corresponding hydroperoxides of alkylaromatic compounds of the general formula (I):

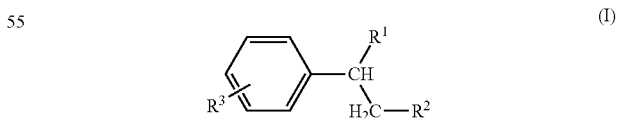

(I)

wherein $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, and $R^3$ represents hydrogen, one or more alkyl groups having from 1 to 4 carbon atoms or a cyclohexyl group. Examples of suitable alkylaromatic compounds are ethyl benzene, cumene, sec-butylbenzene, sec-pentylbenzene, p-methyl-sec-butylbenzene, m 1,4-diphenyl-cyclohexane, sec-hexylbenzene, and cyclohexylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (I) is sec-butylbenzene and is produced by alkylating benzene with at least one $C_4$ alkylating agent under alkylation conditions and in the presence of a heterogeneous catalyst, such as zeolite Beta or more preferably at least one molecular sieve of the MCM-22 family (as defined below). The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (I) is cyclohexylbenzene and is produced by contacting benzene with hydrogen under hydroalkylation conditions in the presence of a hydroalkylation catalyst whereby the benzene undergoes the following reaction to produce cyclohexylbenzene (CHB):

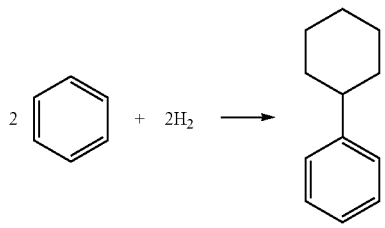

The catalyst employed in the hydroalkylation reaction is a bifunctional catalyst comprising a molecular sieve with an acid function and a hydrogenation metal. Suitable molecular sieves include zeolite beta, zeolite X, zeolite Y and molecular sieves of the MCM-22 family (as defined below). Any known hydrogenation metal can be employed in the hydroalkylation catalyst although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve to produce the catalyst composite. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 50° C. and about 400° C., such as between about 100° C. and about 250° C., while suitable reaction pressures are between about 100 and about 7,000 kPa, such as between about 500 and about 5,000 kPa. Suitable values for the molar ratio of hydrogen to benzene are between about 0.01 and about 100, more particularly between about 0.15:1 and about 15:1, such as between about 0.4:1 and about 4:1, for example between about 0.4 and about 0.9:1. The benzene weight hourly space velocity is normally from about 0.01 to about 100 hr$^{-1}$. The hydroalkylation reaction is exothermic, and so the reaction system must take heat management into account. A preferred method is to recycle a portion of the effluent from the hydroalkylation reactor through a cooling heat exchanger, and mix the cooled recycle stream with the feed. It can also be advantageous to have more than one hydroalkylation bed or reactor, and add hydrogen in stages.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is accomplished by contacting the hydrocarbon substrate with an oxygen-containing gas in the presence of a catalyst comprising a cyclic imide of the general formula (II):

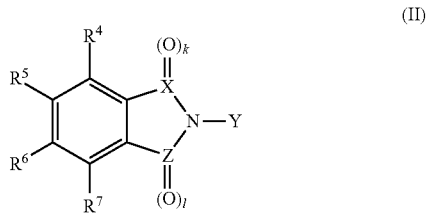

wherein each of $R^4$, $R^5$, $R^6$, and $R^7$ is independently selected from hydrocarbyl and substituted hydrocarbyl radicals having 1 to 20 carbon atoms, or the groups $SO_3H$, $NH_2$, $OH$ and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2.

In one practical embodiment, the cyclic imide catalyst comprises N-hydroxyphthalimide.

The conditions used to effect the oxidation step vary significantly with the type of hydrocarbon substrate to be oxidized, but generally suitable conditions include a temperature between about 20° C. and about 150° C., such as between about 70° C. and about 130° C., and a pressure between about 15 kPa and about 500 kPa, such as between 15 kPa and about 150 kPa.

Depending on the nature of the hydrocarbon substrate, the product of the oxidation step may include one or more of a hydroperoxide, alcohol, ketone, carboxylic acid or dicarboxylic acid of the corresponding hydrocarbon. However, in addition to the desired hydrocarbon oxidation product, the effluent from the oxidation process will contain unreacted cyclic imide catalyst and decomposition products of the cyclic imide. Assuming the catalyst is N-hydroxyphthalimide, these decomposition products include 2-(hydroxycarbamoyl)benzoic acid, phthalic acid, and alkoxy-phthalimide produced according to the following reactions:

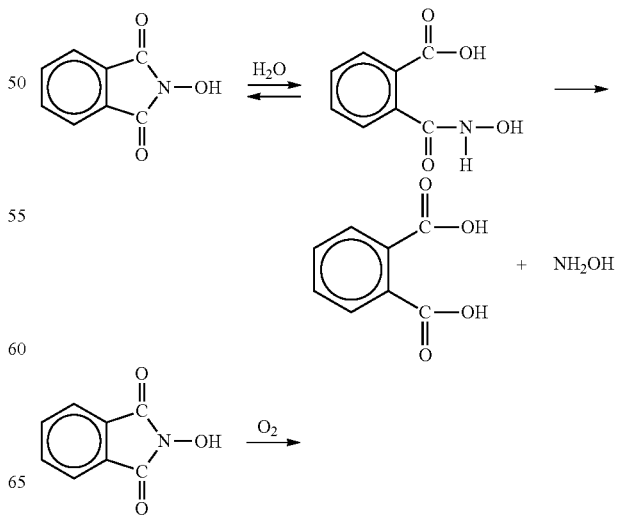

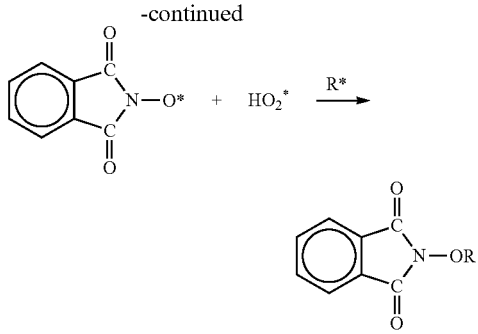

Not only do the unreacted imide catalyst and its decomposition products pose significant problems to downstream reactions, particularly the cleavage step, but also they represent loss of valuable catalyst. Thus the present process captures and removes these materials from the oxidation effluent and feeds the materials to an imide synthesis step so as to generate an improved yield of imide in the synthesis step. The imide catalyst thus recovered and regenerated can then be re-used.

Capture of the unreacted imide catalyst and its decomposition products may involve initially treating the effluent with a base to convert at least part of the unreacted imide and its decomposition products to adducts or salts. The base can be an aqueous solution of a metal carbonate and/or hydrogen carbonate, which will capture the unreacted imide and its acid decomposition products as salts soluble in the aqueous base solution. Such a base will, not, however, react with the ether decomposition products. A more preferred base is therefore a nitrogen-containing base since this will not only produce adducts with the unreacted imide and its acid decomposition products but also with the ether decomposition products. Suitable nitrogen containing bases include (i) ammonia, in which case the adducts are precipitated from the oxidation effluent; (ii) an aqueous ammonium hydroxide or hydroxylamine solution, in which case the adducts dissolve in the aqueous solution; and (iii) pyridine, in which case the adducts are precipitated from the oxidation effluent.

After capture of the unreacted imide catalyst and its decomposition products as adducts and/or salts, the adducts and/or salts are removed from the oxidation effluent, typically by filtration or phase separation, and fed to an imide synthesis reaction. In the imide synthesis reaction, the adducts and/or salts are contacted with at least one reactant selected from hydroxylamine or a salt thereof and an acid or anhydride thereof. Thus, where the imide is N-hydroxyphthalimide, the adducts and/or salts are normally contacted with at least one reactant selected from hydroxylamine or a salt thereof and phthalic acid or phthalic anhydride. For example, when the decomposition product is phthalic acid, hydroxylamine may be added to the decomposition product to convert the phthalic acid back to N-hydroxylphthalimide. In one embodiment, both phthalic acid and hydroxylamine are added to produce additional N-hydroxylphthalimide in addition to regenerating the decomposition products back to N-hydroxylphthalimide.

Typically the imide synthesis reaction is conducted at a pH of less than 7, preferably at a pH of about 2 to about 6 to convert the at least one decomposition product back to N-substituted cyclic imide. In one embodiment, the decomposition product, adduct or salt is converted back to said imide and under conditions to cause said polycarboxylic acid or anhydride to react with said hydroxylamine or salt thereof to produce additional N-substituted cyclic imide. Suitable conditions include a molar ratio of polycarboxylic acid or anhydride to hydroxylamine or salt thereof added to the synthesis reaction of between about 0.5 and about 10.0, for example between about 0.8 and about 2.0, such as between about 1.0 and about 1.8, and a temperature of about 0° C. to about 100° C. for a period of about 0.5 hours to about 24 hours.

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

For example, when the hydrocarbon substrate is isobutane, the oxidation product comprises tertiary butyl hydroperoxide (which is useful as an oxidation reagent and in the production of propylene oxide) and tertiary butanol (which is useful as a gasoline additive).

When the hydrocarbon substrate is cyclohexane, the oxidation product comprises cyclohexyl hydroperoxide, cyclohexanol and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of Nylon 6,6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (I), the product of the oxidation reaction includes a hydroperoxide of general formula (III):

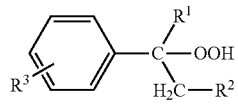

(III)

in which $R^1$, $R^2$ and $R^3$ have the same meaning as in formula (I). Preferably, the hydroperoxide is sec-butylbenzene hydroperoxide, cyclohexylbenzene hydroperoxide or cumene hydroperoxide. This hydroperoxide can then be converted by acid cleavage to phenol or a substituted phenol and an aldehyde or ketone of the general formula $R^1COCH_2R^2$ (IV), in which $R^1$ and $R^2$ have the same meaning as in formula (I). Phenol can of course be reacted with acetone to produce bisphenol A, a precursor in the production of polycarbonates and epoxy resins.

The hydroperoxide cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst. In one practical embodiment, the homogeneous cyclic imide may be converted to heterogeneous catalyst by anchoring or supporting the cyclic imide on a solid material. As an example, the cyclic imide may be anchored on polymer resin through various functionalities such as imido-, amido-, or sulfamido-. As another example, the cyclic imide may be anchored on a solid carrier such as silica gel by a chemical bond through an amino alkyl group. An advantage of the heterogeneous cyclic imide it that it may be easier to separate and recycle as compared to the homogeneous cyclic imide. Also, the heterogeneous cyclic imide can be present in a fixed bed wherein separation of the N-substituted cyclic imide and decomposition products is not necessary. Oxidation reactors may be operated in parallel so that the fixed bed catalyst may be regenerated while off-line.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

Referring to the drawing, FIG. 1 is a flow diagram of the oxidation step and 7, oxidation effluent treatment steps of one embodiment of the present process. In this embodiment, a hydrocarbon stream 7, oxygen stream 8, and an optional make-up imide stream 9 is feed into an oxidation reactor 10 to produce an oxidation effluent. The oxidation effluent 11 and a gaseous or liquid phase base stream 12 are passed to a treatment and separation section 13. In the treatment and separation section 13, the base stream 12 is combined with oxidation effluent to react with at least part of the unreacted imide and its decomposition products to form an adduct or salt. The adduct or salt is then separated from the oxidation effluent and fed as stream 14 to an imide synthesis reactor 15 to produce a regenerated imide. The regenerated imide is typically recycled back to the oxidation reactor via recycle stream 18. The remainder of the oxidation effluent is passed as stream 16 to a downstream reactor 17 where the effluent is converted, typically by oxidation or cleavage, to the desired product.

The invention will now be more particularly described with reference to the following non-limiting Examples.

EXAMPLE 1

Oxidation of Cyclohexylbenzene (CHB) using N-hydroxyphthalimide (NHPI) as the Catalyst 150 g of cyclohexylbenzene from TCI America and 0.16 g NHPI from TCI were weighed into a Parr reactor fitted with a stirrer, thermocouple, gas inlet, sampling port and a condenser containing a Dean Stark trap for water removal. The reactor contents were stirred at 1000 rpm at atmospheric pressure and sparged with nitrogen at a flow rate of 250 cc/minute for 5 minutes. The reactor, while maintained under a nitrogen sparge was then heated to 110° C. When the reaction temperature was reached, the gas was switched from nitrogen to air and the reactor was sparged with air at 250 cc/minute for 4 hours. Samples were taken hourly and analyzed by gas chromatography. After 4 hours, the gas was switched back to nitrogen and the heat was turned off HPLC analysis shows that the NHPI concentration at the end of the oxidation reaction is 926 ppm.

EXAMPLE 2

NHPI Removal Using Ammonium Hydroxide Solution 0.1069 gm $NH_4OH$ aqueous solution (28-32 wt %) was added to 30 gms of the oxidation effluent from Example 1. The mixture was stirred for 15 minutes and then a sample from the organic phase was taken for NHPI analysis. HPLC analysis shows that the NHPI concentration at the end of the $NH_4OH$ treatment is 38.5 ppm and, apart from the reduction in NHPI level, the oxidation effluent composition remains the same before and after the treatment.

EXAMPLE 3

NHPI Removal Using Ammonia Gas

Nitrogen flow was passed through a 30 gm of $NH_4OH$ aqueous solution (28-32 wt %) and the resultant gas was bubbled through 30 gms of the oxidation effluent from Example 1 for 30 minutes. A sample from the organic phase of the effluent was taken for analysis. HPLC analysis shows that the NHPI concentration at the end of the ammonia treatment is 16.5 ppm and, apart from the reduction in NHPI level, the oxidation effluent composition remains the same before and after the treatment.

The above data show clearly that NHPI level in the oxidation effluent was reduced by the $NH_4OH$ and ammonia treatments without decomposing the hydroperoxide product.

In various embodiments, the process relates to:
1. (a) contacting a hydrocarbon with oxygen in the presence of an N-substituted cyclic imide and under conditions to oxidize said hydrocarbon to produce an oxidized hydrocarbon product and at least one decomposition product of the N-substituted cyclic imide; and (b) contacting at least a portion of the at least one decomposition product with a first reactant comprising hydroxylamine or a salt thereof under conditions to convert at least a portion of the at least one decomposition product back to said imide.

2. The process of embodiment 1, further comprising contacting the decomposition product with a second reactant chosen from an acid or anhydride thereof.

3. The process of embodiment 1, further comprising:
(a) treating the oxidized hydrocarbon product, unreacted N-substituted cyclic imide and at least one decomposition product of the N-substituted cyclic imide with a base prior to the contacting (b) to convert at least a portion of said unreacted imide and said decomposition products to an adduct or salt; and (b) removing at least a portion of the adduct or salt from the oxidized hydrocarbon product.

4. The process of embodiment 1, wherein the acid or anhydride thereof is a polycarboxylic acid or anhydride thereof and wherein the polycarboxylic acid or anhydride thereof reacts with said hydroxylamine or salt thereof to produce additional N-substituted cyclic imide.

5. The process of embodiment 1, wherein said hydrocarbon comprises an alkylaromatic compound of general formula (I):

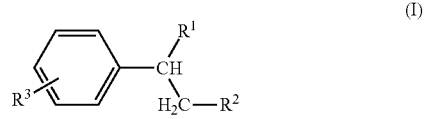

wherein $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, and $R^3$ represents hydrogen, one or more alkyl groups having from 1 to 4 carbon atoms or a cyclohexyl group.

6. The process of embodiment 1, wherein said alkylaromatic compound of general formula (I) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

7. The process of embodiment 1, wherein said oxidized hydrocarbon product comprises a hydroperoxide of general formula (III):

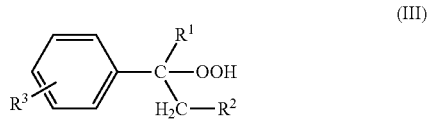

in which $R^1$, $R^2$ and $R^3$ have the same meaning as in formula (I) and the process further comprises cleaving said hydroperoxide to phenol or a substituted phenol and an aldehyde or ketone of the general formula $R^1COCH_2R^2$ (IV), in which $R^1$ and $R^2$ have the same meaning as in formula (I).

8. The process of embodiment 1, wherein said decomposition products comprises phthalic acid.

9. The process of embodiment 1, wherein said decomposition product comprises an alkyoxyphthalimide.

10. The process of embodiment 1, wherein said hydrocarbon comprises cyclohexane, said oxidized hydrocarbon product comprises cyclohexanol and the process further comprises converting the cyclohexanol to adipic acid.

11. The process of embodiment 1, wherein said hydrocarbon comprises cyclohexane, said oxidized hydrocarbon product comprises cyclohexanone and the process further comprises converting the cyclohexanone to caprolactam.

12. The process of embodiment 1, wherein said hydrocarbon comprises iso-butane, said oxidized hydrocarbon product comprises tert-butyl hydroperoxide and the process further comprises using the tert-butyl hydroperoxide as an oxidation catalyst.

13. The process of embodiment 1, wherein said N-substituted cyclic imide obeys the general formula (II):

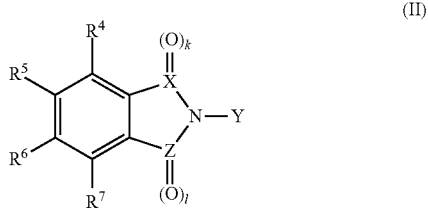

wherein each of $R^4$, $R^5$, $R^6$, and $R^7$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2.

14. The process of embodiment 1, wherein said N-substituted cyclic imide comprises N-hydroxyphthalimide.

15. The process of embodiment 1, wherein said contacting (a) is conducted at a temperature between about 20° C. and about 150° C. and at a pressure between about 15 kPa and about 500 kPa.

16. The process of embodiment 1, wherein said contacting (a) is conducted at a temperature between about 70° C. and about 130° C. and at a pressure between about 15 kPa and about 150 kPa.

17. The process of embodiment 1, wherein said base comprises an inorganic nitrogen compound.

18. The process of embodiment 1, wherein said base comprises ammonia and said adduct is precipitated from said reaction composition.

19. The process of embodiment 1, wherein said base comprises an aqueous ammonium hydroxide solution and said adduct is dissolved in said aqueous solution.

20. The process of embodiment 1, wherein said base comprises an aqueous solution of a metal carbonate and/or hydrogen carbonate and said adduct or salt is dissolved in said aqueous solution.

21. The process of embodiment 1, wherein said base comprises pyridine.

22. The process of embodiment 1, wherein the molar ratio of said polycarboxylic acid or anhydride thereof to said hydroxylamine or salt thereof added to said contacting step (d) is between about 0.5 and about 10.0.

23. The process of embodiment 1, wherein the molar ratio of said polycarboxylic acid or anhydride thereof to said hydroxylamine or salt thereof added to said contacting step (d) is between about 1.0 and about 1.8.

24. The process of embodiment 1, wherein said contacting (d) is conducted at a temperature of about 0° C. to about 100° C.

In various embodiments, the process relates to:

(a) contacting said sec-butylbenzene with an oxygen-containing gas in the presence of an N-substituted cyclic imide and under conditions to oxidize said hydrocarbon and produce an effluent comprising the sec-butylbenzene hydroperoxide, unreacted N-substituted cyclic imide and decomposition products of the N-substituted cyclic imide and;

(b) treating the effluent with a base to convert at least a portion of said unreacted imide and said decomposition products to an adduct or salt;

(c) separating at least a portion of said adduct or salt from said effluent; and (d) contacting at least a portion of the separated adduct or salt with a polycarboxylic acid or anhydride thereof and with hydroxylamine or a salt thereof.

In various embodiments, the contacting (d) occurs at a pH of less than 7 under conditions to convert said adduct or salt back to said imide and to cause said polycarboxylic acid or anhydride thereof to react with said hydroxylamine or salt thereof to produce additional N-substituted cyclic imide.

In various embodiments, the process relates to:

(a) contacting said cyclohexylbenzene with an oxygen-containing gas in the presence of an N-substituted cyclic imide and under conditions to oxidize said hydrocarbon and produce an effluent comprising the cyclohexylbenzene hydroperoxide, unreacted N-substituted cyclic imide and decomposition products of the N-substituted cyclic imide;

(b) treating the effluent with a base to convert at least a portion of said unreacted imide and said decomposition products to an adduct or salt;

(c) separating at least a portion of said adduct or salt from said effluent; and (d) contacting at least a portion of the separated adduct or salt with a polycarboxylic acid or anhydride thereof and with hydroxylamine or a salt thereof In various embodiments, the contacting (d) occurs at a pH of less than 7 under conditions to convert said adduct or salt back to said imide and to cause said polycarboxylic acid or anhydride thereof to react with said hydroxylamine or salt thereof to produce additional N-substituted cyclic imide.

In various embodiments, the process relates to:

(a) contacting the hydrocarbon feedstock with oxygen in the presence of an N-substituted cyclic imide under conditions sufficient to oxidize at least a portion of the hydrocarbon feedstock, to produce an effluent including at least an oxidized feedstock, and at least one decomposition product of the N-substituted cyclic imide;

(b) removing from the effluent at least a portion of the decomposition product of the N-substituted cyclic imide;

(c) contacting the removed portion of the decomposition product of the N-substituted with at least one reactant selected from an acid or anhydride thereof and hydroxylamine or a salt thereof to convert at least a portion of the decomposition product back to said imide; and (d) recycling the imide resulting from step (c) to step (a).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for oxidizing a hydrocarbon, the process comprising:
   (a) contacting a hydrocarbon with oxygen in the presence of an N-substituted cyclic imide and under conditions to oxidize said hydrocarbon to produce an oxidized hydrocarbon product and at least one decomposition product of the N-substituted cyclic imide;
   (b) contacting at least a portion of the at least one decomposition product with: (1) a first reactant comprising one or both of hydroxylamine and a salt thereof; and (2) a second reactant comprising one or both of polycarboxylic acid and an anhydride thereof under conditions to convert at least a portion of the at least one decomposition product back to said imide; wherein the first reactant reacts with the second reactant to produce additional N-substituted cyclic imide.

2. The process of claim 1, wherein the contacting (a) further forms unreacted N-substituted cyclic imide and the process further comprises:
   (i) treating the oxidized hydrocarbon product, unreacted N-substituted cyclic imide and at least one decomposition product of the N-substituted cyclic imide with a base prior to the contacting (b) to convert at least a portion of said unreacted imide and said decomposition product to an adduct or salt; and
   (ii) removing at least a portion of the adduct or salt from the oxidized hydrocarbon product.

3. The process of claim 1, wherein the second reactant comprises one or both of phthalic acid and a salt thereof.

4. The process of claim 1, wherein said hydrocarbon comprises an alkylaromatic compound of general formula (I):

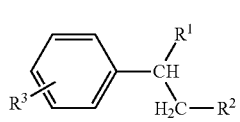

wherein $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, and $R^3$ represents hydrogen, one or more alkyl groups having from 1 to 4 carbon atoms or a cyclohexyl group.

5. The process of claim 4, wherein said alkylaromatic compound of general formula (I) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

6. The process of claim 1, wherein said oxidized hydrocarbon product comprises a hydroperoxide of general formula (III):

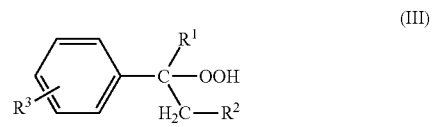

in which $R^1$, $R^2$ and $R^3$ have the same meaning as in formula (I) and the process further comprises cleaving said hydroperoxide to phenol or a substituted phenol and an aldehyde or ketone of the general formula $R^1COCH_2R^2$ (IV), in which $R^1$ and $R^2$ have the same meaning as in formula (I).

7. The process of claim 1, wherein said decomposition product comprises phthalic acid.

8. The process of claim 1, wherein said decomposition product comprises an alkoxy-phthalimide.

9. The process of claim 1, wherein said hydrocarbon comprises an alkane, such as isobutane, or cycloalkane, such as cyclohexane.

10. The process of claim 1, wherein said N-substituted cyclic imide obeys the general formula (II):

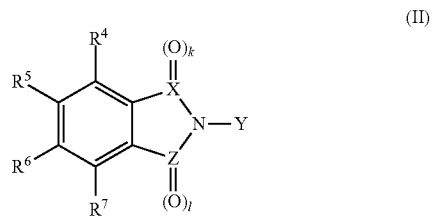

wherein each of $R^4$, $R^5$, $R^6$, and $R^7$ is independently selected from hydrocarbyl and substituted hydrocarbyl radicals having 1 to 20 carbon atoms, or the groups $SO_3H$, $NH_2$, $OH$ and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2.

11. The process of claim 1, wherein said N-substituted cyclic imide comprises N-hydroxyphthalimide.

12. The process of claim 1, wherein said contacting (a) is conducted at a temperature between 20° C. and 150° C., preferably between 70° C. and 130° C. and at a pressure between 15 kPa and 500 kPa, preferably between 15 kPa and 150 kPa.

13. The process of claim 2, wherein said base comprises an inorganic nitrogen compound.

14. The process of claim 13, wherein said base comprises ammonia and said adduct is precipitated from said reaction composition.

15. The process of claim 2, wherein said base comprises an aqueous ammonium hydroxide solution and said adduct is dissolved in said aqueous solution.

16. The process of claim 2, wherein said base comprises an aqueous solution of a metal carbonate and/or hydrogen carbonate and said adduct or salt is dissolved in said aqueous solution.

17. The process of claim 2, wherein said base comprises pyridine.

18. The process of claim 1, wherein the molar ratio of said second reactant to said first reactant is between 0.5 and 10.0.

19. The process of claim 1, wherein said contacting (b) is conducted at a temperature of 0° C. to 100° C.

20. A process for oxidizing sec-butylbenzene to a sec-butylbenzene hydroperoxide, the process comprising:
- (a) contacting said sec-butylbenzene with an oxygen-containing gas in the presence of an N-substituted cyclic imide and under conditions to oxidize said sec-butylbenzene and produce an effluent comprising the sec-butylbenzene hydroperoxide, unreacted N-substituted cyclic imide and decomposition products of the N-substituted cyclic imide and;
- (b) treating the effluent with a base to convert at least a portion of said unreacted imide and said decomposition products to an adduct or salt;
- (c) separating at least a portion of said adduct or salt from said effluent; and
- (d) contacting at least a portion of the separated adduct or salt with a polycarboxylic acid or anhydride thereof and with hydroxylamine or a salt thereof under conditions to convert at least a portion of the separated adduct or salt back to said N-substituted cyclic imide; wherein the polycarboxylic acid or anhydride thereof reacts with the hydroxylamine or salt thereof to produce additional N-substituted cyclic imide.

21. The process of claim 20, wherein the contacting (d) occurs at a pH of less than 7.

22. A process for oxidizing cyclohexylbenzene to a cyclohexylbenzene hydroperoxide, the process comprising:
- (a) contacting said cyclohexylbenzene with an oxygen-containing gas in the presence of an N-substituted cyclic imide and under conditions to oxidize said cyclohexylbenzene and produce an effluent comprising the cyclohexylbenzene hydroperoxide, unreacted N-substituted cyclic imide and decomposition products of the N-substituted cyclic imide;
- (b) treating the effluent with a base to convert at least a portion of said unreacted imide and said decomposition products to an adduct or salt;
- (c) separating at least a portion of said adduct or salt from said effluent; and
- (d) contacting at least a portion of the separated adduct or salt with a polycarboxylic acid or anhydride thereof and with hydroxylamine or a salt thereof under conditions to convert at least a portion of the separated adduct or salt back to said N-substituted cyclic imide; wherein the polycarboxylic acid or anhydride thereof reacts with the hydroxylamine or salt thereof to produce additional N-substituted cyclic imide.

23. The process of claim 22, wherein the contacting (d) occurs at a pH of less than 7.

24. A process for oxidizing a hydrocarbon feedstock, the process comprising the steps of:
- (a) contacting the hydrocarbon feedstock with oxygen in the presence of an N-substituted cyclic imide under conditions sufficient to oxidize at least a portion of the hydrocarbon feedstock, to produce an effluent including at least an oxidized feedstock, and at least one decomposition product of the N-substituted cyclic imide;
- (b) removing from the effluent at least a portion of the decomposition product of the N-substituted cyclic imide;
- (c) contacting the removed portion of the decomposition product of the N-substituted with at least one reactant selected from a polycarboxylic acid or anhydride thereof and hydroxylamine or a salt thereof to convert at least a portion of the decomposition product back to said imide and to produce additional imide; and
- (d) recycling the imide resulting from step (c) to step (a).

\* \* \* \* \*